United States Patent [19]

Chandra

[11] Patent Number: 4,847,297

[45] Date of Patent: Jul. 11, 1989

[54] USE OF PENICILLAMINE FOR TREATING IMMUNE DAMAGING ILLNESSES

[75] Inventor: Prakash Chandra, Frankfurt am Main, Fed. Rep. of Germany

[73] Assignee: Degussa Aktiengesellschaft, Frankfurt am Main, Fed. Rep. of Germany

[21] Appl. No.: 170,638

[22] Filed: Mar. 16, 1988

Related U.S. Application Data

[63] Continuation of Ser. No. 860,462, May 7, 1986, abandoned.

[30] Foreign Application Priority Data

Jun. 8, 1985 [DE] Fed. Rep. of Germany ....... 3520624

[51] Int. Cl.$^4$ .......................................... A61K 31/195
[52] U.S. Cl. ..................................... 514/562; 514/934
[58] Field of Search ................................ 514/562, 934

[56] References Cited

U.S. PATENT DOCUMENTS 4,487,780 12/1984 Scheinberg .......................... 514/562

FOREIGN PATENT DOCUMENTS 585413 2/1947 United Kingdom .
1424432 2/1976 United Kingdom .

OTHER PUBLICATIONS

Chemical Abstracts 87:95836k(LIU) 1977.
"Treatment of HTLV-III/LAV-infected Patients with D-Penicillamine," Schulof et al, Arzneim.-Forsch./-Drug Res. 36(II), No. 10(1986) pp. 1531-1534.
"Prolonged Antiviral Activity of D-Penicillamine in Human Immunodeficiency Virus-Infected Homosexual Men", Scheib et al, The American Journal of Medicine, vol. 83, Sep. 1987, p. 608.
"View of AIDS Too Narrow, Scientists Say", The Washington Post, Jan. 13, 1988.

*Primary Examiner*—Leonard Schenkman
*Attorney, Agent, or Firm*—Cushman, Darby & Cushman

[57] ABSTRACT

The invention is directed to the use of penicillamine for controlling illnesses, e.g., AIDS, which are distinguished by an immune deficiency syndrome.

7 Claims, 2 Drawing Sheets

USE OF PENICILLAMINE FOR TREATING IMMUNE DAMAGING ILLNESSES

This is a continuation of application Ser. No. 860,462, filed May 7, 1986, which was abandoned upon the filing hereof.

BACKGROUND OF THE INVENTION

Penicillamine is a non-physiological aminoacid, namely a dimethyl derivative of cysteine.

Penicillamine can occur in two enantiomeric forms. One enantiomer form, the D-penicillamine, can be produced from natural penicillin by hydrolysis or can be produced completely synthetically.

The completely synthetic D-penicillamine can be obtained, for example, by racemic resolution of D,L-penicillamine with the help of optically active bases such as, for example, brucine, d-pseudoephedrine or l-ephedrine (see "The Chemistry of Penicillin" 1949 Princeton University Press; compare British Pat. No. 585413, U.S. Pat. No. 2,450,784, Belgian Pat. No. 7385207) or l-norephedrin (German Pat. No. 2138122).

An advantage of D-penicillamine over other -SH compounds, as well as over other cysteine derivatives, is its relative stability in the metabolism, through which its activity is well developed.

D-penicillamine since about 1960 has been employed in the therapy of various illnesses, thus, for example, in the progressive chronic polyarthritis, heavy metal poisonings, chronic-aggressive hepatitis, cirrhosis of the liver, cystinuria, cystine stones, sclerodermia, Morbus Wilson, Morbus Waldenstrom, schizophrenic deficiency, arteriosclerotic disorders, Lupus erythematodes and fibrosis of various genesis.

In the previous long time use of D-penicillamine its toxicology and pharmacokinetics have become well known so that even at a high dosage therapy the side effects associated therewith and the incompatibilities are controlled.

SUMMARY OF THE INVENTION

It has now been found D- and L-penicillamine as well as the D,L-racemate can also be employed for the therapy of illnesses which are distinguished by an immune deficiency syndrome. An illness with advancing more severe immune deficiency which via the development of tumors and infections lead to death is the Acquired Immune Deficiency Syndrome (AIDS). The illness (disease) was first made known in 1981 and in the meantime a viral genesis could be detected. In the search for the causes of the diseases of the immune deficiency syndrome, there was found a disturbance of the immune regulation and immune defense. The ratio of $T_4$ (helper cells) to $T_8$ (suppressor cells) is disturbed. In the year 1983, there were isolated the lymphadenopathy virus (LAV-I) and in the year 1984 there was isolated human-T-cell-leukemia virus, the HTLV-III virus, a virus of the retroviral group and which virus was proven to be the cause of AIDS. The LAV-I virus and the HTLV-III virus were found by two different investigating groups and were regarded as practically the same. To eliminate confusion these viruses are now referred to by the name HIV. The target cells of the AIDS virus are cells of the immune system. The infection remains for months to years unnoticed until finally symptoms occur, which at first appear unspecific, but in their combination and long persistence, together with a frequently arising lymphadenopathy, can be a clear indication of an infection with this virus. In the further progress of the infection, there can be severe functional disturbances of the cellular immune defense.

As a result, there occur infections with opportunistic stimulations and/or tumors, such as, for example, Kaposi sarcoma and non-Hodgkin lymphoma. The infections with opportunistic stimulations, parasites and/or the occurrence of tumors determine the progress and termination of the AIDS disease. Patients in these stages die within 36 months to an extent of above 80% due to these complications.

The following people have an increased risk of getting AIDS disease: homosexual men with frequently changing intimate partners, those dependent on i.v. dispensed drugs (fixes), heterosexual intimate partners of those who are infected and ill, immigrants or tourists to Haiti, the Carribean or equatorial Africa (e.g., Zaire), hemophiliac patients who receive concentrates of clotting factors (e.g., Factor VIII), babies of infected mothers, receivers of AIDS-virus-containing blood.

It has now been found in vitro that penicillamine can greatly inhibit the virus replication and in addition shows no toxicity to the normal cell growth. The inhibition is shown both with D- and L-penicillamine and with the D,L-racemate. At a concentrate of 20 μg/ml the replication of HTLV-III—virus (LAV-I-virus) is prevented in a cell culture with L-penicillamine to an extent of about 95% and with D-penicillamine to about 80%. At a concentration of 40 μg/ml, the effectiveness of both L-penicillamine and D-penicillamine in vitro is nearly 100%.

It is known that L-penicillamine and the D,L-racemate exhibit a higher toxicity so that for use on human the D-enantiomer is preferred.

Naturally, not only patients with clinical AIDS-symptons can be treated with the new medicament. Patients who are already infected in whose blood corresponding antibodies have been detected, without already showing the illness picture can be treated in the same manner.

The medicines which contain penicillamine as well as mixtures of it with other pharmaceutically active materials, as well as in a given case with addition of further pharmaceutical carriers can be used enterally, parenterally, vially, locally, perlingually as well as in the form of sprays.

The dispensation can be carried out, for example, in the form of tablets, capsules, pills, dragees, plugs, salves, jellies, creams, powders, dusts, aerosols, or in liquid form. As liquid forms of the use there can be employed, for example, oily or alcoholic or aqueous solutions as well as suspensions and emulsions.

Especially there are used the following medicaments:

(a) Oral forms of medicine such as granulates, tablets, dragees, capsules, etc., as well as solutions, emulsions, suspensions and the like. Thereby the dosage of D-penicillamine, for example, 125 mg, 250 mg, 300 mg, or 500 mg per individual dosage.

(b) Parenteral forms of medicine, for example, for intravenous or intramuscular injection with, for example, an active material dosage of 50 to 2000 mg per individual dosage.

Hereby penicillamine can be present, for example, in the form of D-penicillamine hydrochloride and/or D-penicillamine paratoluenesolfonate.

(c) Forms of the medicine for rectal and vaginal application. Dosage, for example, of 50 to 1000 mg per individual dosage.

The production of the medicine can be carried out using the known and customary pharmaceutical carriers and diluents as well as other customary assistants. These types of carriers and assistants are set forth, for example, in Ullmann's Encyklopadie der technischen Chemie, Vol. 4 (1953), pages 1–39; Journal of Pharmaceutical Sciences 52 (1963), pages 918 et seq.; H. v. Czetsch-Lindenwald, Hilfsstoffe fur Pharmazie und angrenzende Gebiete; Phar. Ind. 2 (1961), pages 72 et seq.; Dr. H. P. Fiedler, Lexicon angrenzende Gebiete, Cantor Kg. Aulendorf in Wurttemberg (1971).

Examples of such materials include gelatin, natural sugars such as sucrose or lactose, lecithin, pectin, starch (for example cornstarch), alginic acid, tylose, talc, lycopodium, silica (for example collodial silica), glucose, cellulose, cellulose derivatives for example, cellulose ethers in which the cellulose hydroxyl group are partially etherified with lower aliphatic alcohols and/or lower saturated oxyalcohols (for example, methyl hydroxypropyl cellulose, methyl cellulose, hydroxyethyl cellulose), stearates, e.g., methylstearate and glyceryl stearate, magnesium and calcium salts of fatty acids with 12 to 22 carbon atoms, especially saturated acids (for example, calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono, di, and triglycerides of saturated fatty acids ($C_{12}H_{24}O_2$ to $C_{18}H_{36}O_2$ and their mixtures), e.g. glyceryl monostearate, glyceryl disterate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol disterate, glycol dilaurate, glycol diacetate, monoacetin, triacetin, glyceryl oleate, ethylene glycol stearate; such esters of polyvalent alcohols can in a given case be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, water, dimethyl sulfoxide, etc.

In the production of solutions, it can be necessary to produce the desired D-penicillamine concentration to employ organic solvents alone or in admixture with water. As physiologically compatible organic solvents, there can be used, for example, mono or polyhydric alcohols such as ethanol, isopropanol, butanol, ethylene glycol, propylene glycol, glycerine, diglycerine, triglycerine, polyglycerines (having 4 to 12 glycerine units), polyethylene glycols, e.g., diethylene glycol or triethylene glycol, polypropylene glycols, e.g., dipropylene glycol as well as their ethers with lower aliphatic alcohols, e.g., the mono methyl and mono ethyl ether, ethylene glycol, diethylene glycol and propylene glycol, as well as the esters with lower aliphatic carboxylic acids, e.g., ethylene glycol monoacetate, diethylene glycol monoacetate, aliphatic carboxylic acid amides (containing 1 to 10 carbon atoms), e.g., formamide, acetamide, propionamide, butyramide, decanoamide, N-alkyl substituted carboxylic acid amides such as dimethylformamide or dimethylacetamide, etc.

Furthermore, there can be added preservatives, stabilizers, buffers, for example, calcium hydrogen phosphate, collodial aluminum hydroxide, taste correctives, antioxidants and complex formers (for example, ethylene diamine tetraacetic acid, and the like, see also U. Olthoff and R. Huttenrauch, Die Pharmazie Vol. 26 No. 4 page 217 (1971). In a given case for stabilization of the D-penicillamine, there is established with physiologically compatible acids or buffers a pH in the range of 4.0–4.5.

As antioxidants, there can be used, for example, sodium metabisulfite, as preservative, for example, sorbic acid, p-hydroxybenzoic acid ethyl ester and the like. The addition of carbonyl compounds generally is not suitable.

The pharmacological and galenical handling of the compounds of the invention is carried out according to the customary standard methods (see, for example, Hagers Handbuch der Pharmazeutischen Praxis, 4th new edition Vol. VII Part A; Arzneiformen).

The addition of other medically active materials inert to D-penicillamine, above all analgetics, antihistamines, antiphlogistics, spasmolytics, geriatrics, liver therapeutics, vitamins, trace elements, and steroids especially is possible or favorable.

Preferably, the additional materials should possess no optical activity on their own, since through this it is easier to control the rotary value of the D-penicillamine.

The pharmaceutical preparations generally contain between 0.5 to 100 weight percent D-penicillamine.

It is proper to use, for example, 4 times daily 1 to 6 tablets, preferably 2 to 4 tablets, having a content of 125 mg to 500 mg, preferably 300 mg, of active material (commercial preparation Trolovol® Bayer/Degussa Pharma group). The dosaging at the beginning of the treatment should be relatively low and after about two weeks increased according to the medical necessity. With intravenous injection, it is proper to employ 1–2 times daily a 10 ml ampoule containing 1000 mg of material. It is known from research that D-penicillamine is bound to plasma proteins (preponderantly albumen). Since the concentration of the free, i.e., not protein bound D-penicillamine obviously increases with increasing dosage, for therapeutic practice there is the necessity of not having a too low dosage. The medicament after oral administration is resorbed about 60% within 2 to 3 hours. As is true with other aminoacids, it is distributed relatively quickly over the entire organism, and the non-eliminated fraction has a half-life time of 75 respectively 90 hours. Elimination is carried out predominantly via the kidneys, the greatest part as disulfide, up to 10% in unchanged form.

The accute toxicity of the D-penicillamine on the mouse (expressed by the $LD_{50}$ mg/kg; method according to Miller & Tainter, Proc. Soc. Exper. Biol. a Med. Vol. 57 (1944), pages 261 et. seq.) is for example with oral application between 7000 and 10,500 mg/kg.

In place of the D-penicillamine base, there can also be used the salts obtained by means of customary methods.

As acid components for the salts there can be employed the customary pharmacologically usable acids, such as, for example, hydrochloric acid, hydrobromic acid, sulfuric acid, acetic acid, citric acid, succinic acid, maleic acid, fumaric acid, lactic acid, para toluenesulfonic acid, and the like.

Especially there can be used, for example, the anions of the following acids: HBr, HCl, HI, $HNO_3$, $H_2SO_4$ ($SO_4^=$); $H_3PO_4$, ($HPO_3^=$); camphor sulfonic acid, aliphatic or aromatic sulfonic acids, for example, $C_1$–$C_6$-alkylsulfonic acids (for example, methanesulfonic acid, ethanesulfonic acid, propanesulfonic acid or hexanesulfonic acid), benzenesulfonic acid or naphthalenesulfonic acid, which in a given case are substituted by one or two methyl groups (toluenesulfonic acid, especially o- or p-toluenesulfonic acid; aliphatic $C_2$–$C_4$-monocarboxylic acids, which in a given case are substituted by one, two, or three halogen atoms (especially Cl, F) (for example, acetic acid, propionic acid, butyric acid, chloroacetic acid, dichloroacetic acid, trichloroacetic acid, trifuloroacetic acid; aliphatic $C_2$–$C_{11}$-dicarboxylic acids, which in a given case contain a double bond (for example, oxalic acid, malonic acid, malonic acid substituted in the 2-position by one or two $C_1$–$C_4$-alkyl groups, e.g., 2-methylmalonic acid, 2,2-dimethylmalonic acid, 2-propylmalonic acid, maleic acid, fumaric acid, succinic acid, decanedioic acid); aliphatic monohydroxy and dihydroxy monocarboxylic acids having 2 to 6, especially 2 to 3 carbon atoms, whereby there are preferably used—monohydroxycarboyxlic acids such as lactic acid, glyceric acid, or glycolic acid; aliphatic monohydroxy- and dihydroxy di- and tricarboxylic acids having 3 to 8 carbon atoms, especially 3 to 6 carbon atoms such as tartronic acid, malic acid, tartaric acid, malonic acid, which is substituted on the middle carbon atom by a hydroxy group and in a given case also by a $C_1$–$C_4$-alkyl group, isocitric acid or citric acid; phthalic acid, which in a given case is substituted by a carboxyl group (especially in the 4-position); gluconic acid; glucuronic acid; 1,1-cyclobutanedicarboxylic acid; organophosphorus acids, such as aldose and ketosephosphoric acids (for example, the corresponding mono- and diphosphoric acids) for example, aldose-6-phosphoric acids such as D- or L-glucose-6-phosphoric acid, —D-glucose-1-phosphoric acid, D-fructose-6-phosphoric acid, D-galactose-6-phosphoric acid, D-ribose-5-phosphoric acid, D-fructose-1,6-diphosphoric acid; glycerine phosphoric acids (in which case the phosphonic acid radical can be bound on a terminal or middle glycerine oxygen atom) such as α-D,L-glycerine phosphoric acid; β-glycerine phosphoric acid; N-phosphonoacetyl-aspartic acid (for example, L-aspartic acid).

It is recommended to make investigations of the blood picture and the urine before beginning the treatment with D-penicillamine. During the therapy corresponding medicine control investigations are undertaken in known manner. The effect of the treatment in addition to the improvement of the clinical symptoms is especially recognized through detecting the immunological parameter (ratio of $T_4$ helper cells to $T_8$ suppressor cells).

Pharmaceutical preparation containing completely synthetic D-penicillamine, for example, are described in British Pat. No. 1,424,432, the entire disclosure of which is hereby incorporated by reference and relied upon.

The process can comprise, consist essentially of, or consist of the recited steps employing a composition comprising, consisting essentially of, or consisting of the stated materials.

DETAILED DESCRIPTION

Carrying Out of Experiments

HTLV-III virus infection of H9 cells (human T-cell line of a leukemia patient of the National Cancer Institute, Bethesda, Md., USA); the H9 cells were trreated with Polybrene (Hexadimethrine bromide) (2 μg/ml) for 30 minutes at 37° C., subsequently the Polybrene was washed out and the cells were infected with $2 \times 10^8$ HTLV virus particles per $4 \times 10^5$ H9 cells. Before the infection, the virus was incubated with the material at various concentrations for 45 minutes at 37° C. For controls, the virus was incubated under the same experimental conditions but without addition of the material. The cell cultures were analyzed on the 4th day after infection as follows:

Immunofluorescence analysis: The effect of D- and L-penicillamine on the propagation of the HTLV-III virus in H9 cells was determined by measuring the proteins p15 and p24 (molecular weight 15,000 respectively 24,000) present in HTLV-III. The immunofluorescence analysis was carried out on fixed methanol:acetone (1:1) cells using monoclonal antibodies (National Cancer Institute USA) against HTLV-III p15 and p24. The infected cells treated with or without penicillamine were secured on toxoplasmosis glass slides. After 30 minutes treatment with methanol-acetone (1:1) at room temperature, the glass slides were stored in closed plastic containers at −20° C. until use. The monoclonal antibodies were added to duplicate wells, incubated at room temperature in a moist chamber for 1 hour and washed with PBS (phosphate buffered saline) solution containing 0.25% Triton X-100 for two hours. The cells were then exposed to goatantimouse IgG (Capell Labs.) bound with fluorescein (FITC) for 1 hour and washed with PBS buffer solution containing 0.25% Triton X-100 overnight. The glass sides were mounted with 50% glycerine and the cell fluorescence observed with a Zeiss fluorescence microscope.

The effect of D- and L-penicillamine on the propagation of HTLV-III in H9 cells was determined through the function of the material concentration by the formation of the viral proteins p15 (FIG. 1) and p24 (FIG. 2) in an immunofluorescence assay with monoclonal antibodies.

Figure 1:
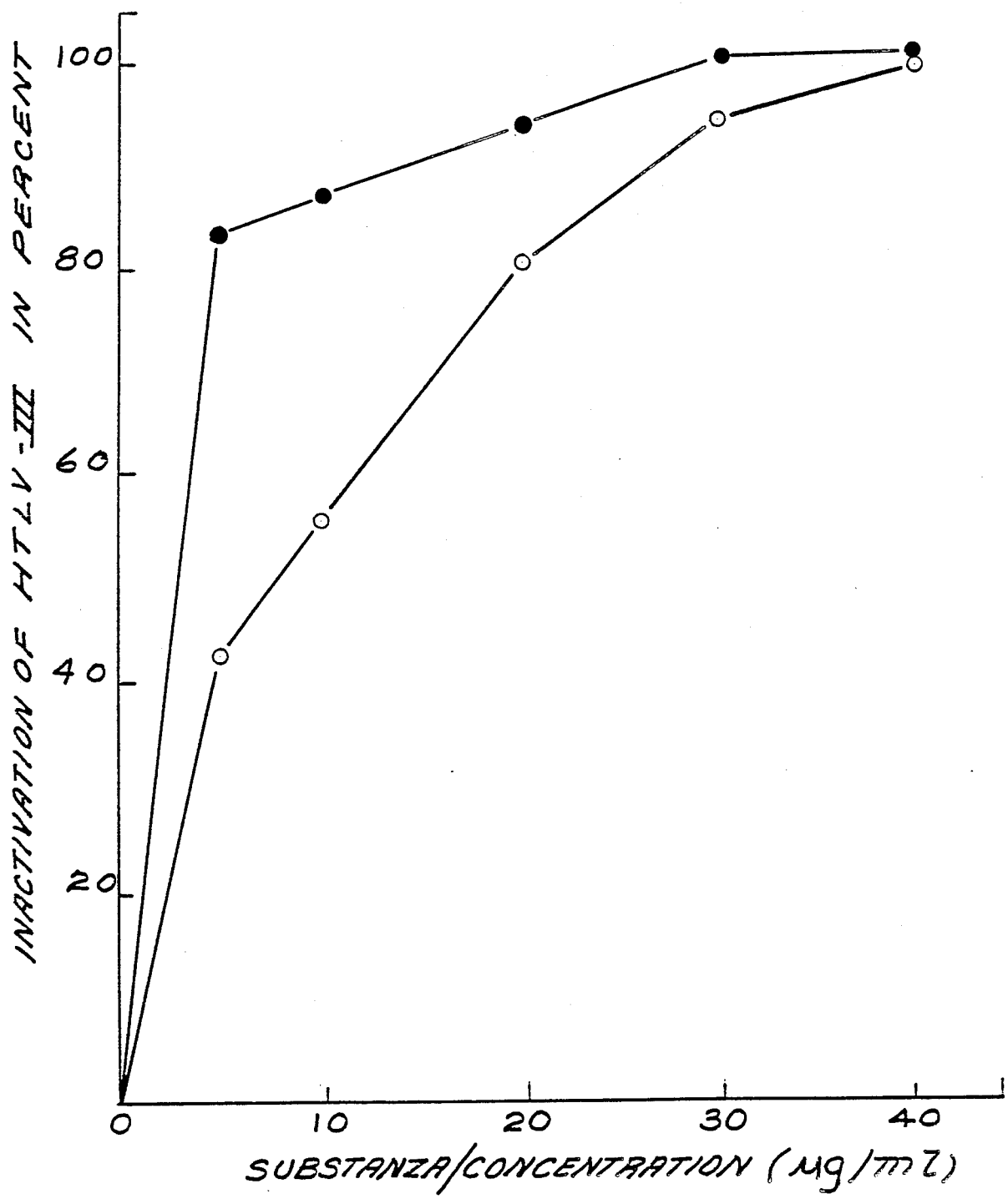
FIG. 1 is a graph of the effect of D- and L-penicillamine on the propagation of HTLV-III in H9 cells through the function of the concentration determined by the formation of the viral protein 15.

FIG. 1 shows a concentration dependent prevention of the formation of p15 virus protein both with L-penicillamine (black dots) and with D-penicillamine (clear dots). At lower concentration L-penicillamine is more effective than D-penicillamine. In order to reach an inhibition of 98.5% to 99.4%, a concentration of 40 μg/ml for both isomers is needed.

Figure 2:
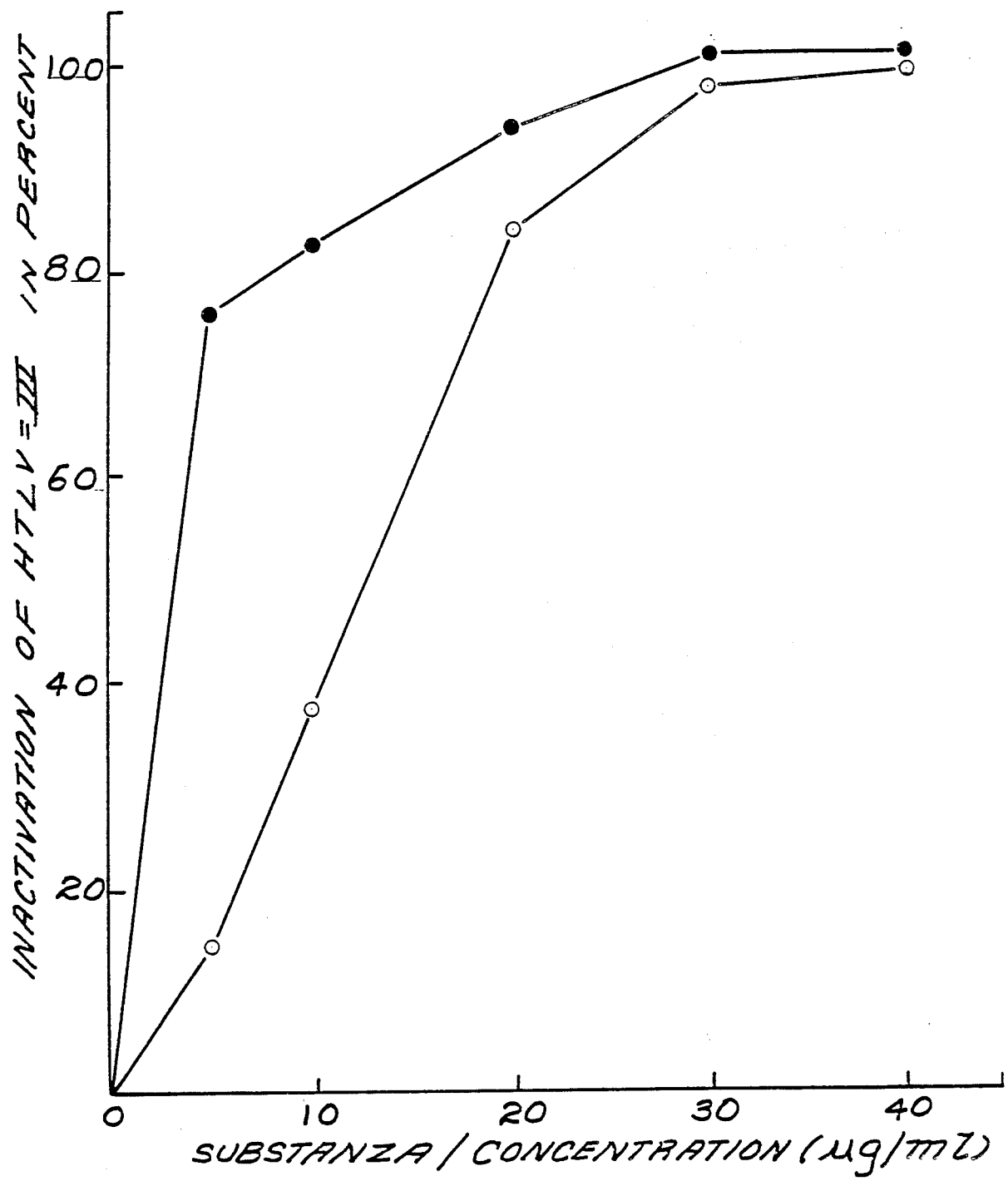
FIG. 2 is a similar graph where the determination was by the formation of viral protein p24.

FIG. 2 shows the inactivation of HTLV-III by D- and L-penicillamine with the help of immunofluorescence analysis using monoclonal antibodies against viral protein p24. Both materials prevent the formation of p24 in the same manner as with viral protein p15. In order to attain a complete inactivation of the viral replication with the isomers, there is needed a concentration of 40 μg/ml.

In order to show the selectivity of the effect on the replication of HTLV-III virus, the effect of D- and L-penicillamine on the growth of H9 cells can be examined. The effects of the two materials on infected and non-infected cells is shown in Table 1.

TABLE 1

Effect of D- and L-Penicillamine on the Growth of Infected and Non-Infected H9 Cells

| Experiment | Number of cells/ml × $10^{-6}$ | | | |
|---|---|---|---|---|
| | non-infected 1.24 | | Infected 0.18 | |
| μg/ml | DP* | LP* | DP | LP |
| 20 | | | | |
| 30 | | | 0.27 | 0.35 |
| 40 | 1.30 | 1.31 | 0.35 | 0.38 |
| 100 | 1.30 | 1.31 | 0.8 | 0.98 |
| 500 | 0.84 | 0.94 | | |
| 750 | 0.18 | 0.53 | | |

*DP and LP indicate D- and L-Penicillamine

The number of cells was determined 4 days after the experiment began.

D-penicillamine prevents the growth of non-infected cells only from a concentration over 100 μg/ml. At a concentration of 500 μg/ml D-penicillamine shows an inhibition of cell growth of 32%, at the same concentration L-penicillamine shows an inactivation of cell growth of approximately 24%, material concentrations of more than 50 μg/ml prevent the growth of non-infected cells very greatly.

The effect of D- and L-penicillamine on the growth of infected cells in Table 1 shows the following:

4 days after the infection with the HTLV-III virus the number of H9 cells is reduced from $1.24 \times 10^6$ to $0.18 \times 10^6$. In the presence of D- and L-penicillamine, there is found with increasing concentration a considerable increase of the cell number. This means that both materials have a protective effect on T-cells.

In general, the amount of penicillamine in the blood of the patient is between 10 and 400, preferably between 30 and 300 respectively 40 to 200, especially 40 to 100 respectively 40 to 50 micrograms per ml of blood. In order to attain this serum concentration with humans, with peroral application the following dosage is recommended.

0.5 to 3 grams, especially 0.9 grams to 2.1 grams, preferably 1.5 grams to 2 grams of D-penicillamine per day upon awakening, whereby a dosage of 3 grams per day can be given only over a time span of about 1 week, or 2 grams per day over a time span of 12 months. With intravenous application, there is recommended the giving of 1 gram to 2 grams of active material per day upon awakening, whereby from 0.5 to 1.5 grams, preferably 1 gram of D-penicillamine is dispensed in a suitable solution. With patients in infancy, the recommended dosages are reduced accordingly. The dosages also can be dispensed individually in smaller doses over the day, for example, with peroral application 1 to 6 times daily, preferably 2-4 times daily 200 mg to 500 mg D-penicillamine. An overdosage of about 4 grams of D-penicillamine over a long time span should be avoided.

All amounts added in the application refer to the penicillamine base. When using penicillamine salts, the corresponding amounts in each case are correspondingly increased.

EXAMPLE 1

Tablets 300 grams of D-penicillamine were mixed in a suitable mixer with 0.25 grams of ethylenediaminetetraacetic acid disodium salt, 30 grams of cornstarch, and 5.25 grams of highly dispersed silica and wet granulated with a solution which consisted of 12 grams of Luviskol VA 64 (high polymeric vinyl pyrrolidone/vinyl acetate copolymer in a ratio of 60:40), 102 grams of isopropanol and 6 grams of demineralized water. The wet mass is then passed through a suitable granulating machine and dried. The outer phase consisting of 90 g of corn starch, 50 g of cellulose, 10 g of highly disperse silica and 1.5 g of magnesium stearate, is then added to and homogeneously mixed with the dry, sifted granulate. The mixture is then pressed into tablets weighing 500 mg.

EXAMPLE 2

Lacquered Tablets

The tablets produced according to Example 1 are coated with a protective film soluble in gastric juices to protect them against the effect of moisture and atmospheric oxygen and also to conceal the unpleasant taste and odour of the D-penicillamine. The protective film can be applied to the tablets in a dragee vesel or suitable fluidised-bed arrangement.

87.5 ml of a suspension of the following composition are applied per 500 g=1000 tablets in the usual way (for example, in a Wurster machine):

| | in % by weight/weight |
|---|---|
| ethyl cellulose* | 2% |
| hydroxypropyl cellulose* | 1% |
| polyethylene glycol 5/6000 | 2.5% |
| glycerol | 0.5% |
| titanium dioxide | 3.5% |
| talcum | 1.5% |
| isopropanol | 44.5% |
| 1,1,1-trichloroethane | 44.5% |
| | 100.0% |

*Various ethyl and hydroxypropyl celluloses of the kind marketed by the Dow, Hercules and Syntana organisations under the names: Ethocel and Klucel, can be used as film formers.

EXAMPLE 3

Production of Gelatin Insertion Capsules With D-Penicillamine HCl 185 g of D-penicillamine HCl, 3 g of highly disperse silica and 9 g of tricalcium-phosphate are mixed and granulated in known manner with 60 g of a solution consisting of 5% of hydroxypropylmethyl cellulose, 75% by weight/volume of ethanol and 20% of demineralised water. The dry granulate is packed into gelatin insertion capsules in individual quantities of 200 mg. 1 capsule contains 185 mg of d-penicillamine HCl.

EXAMPLE 4

Production of D-penicillamine Dry Ampoules 123 g of D-penicillamine HCl (corresponding to 100 g of D-penicillamine) are dissolved under gentle heat on a water bath with distilled water to make a total volume of 500 ml. The solution is passed through a sterilising filter and introduced in 5 ml portions into suitable multidose ampoules. The aqueous content of the ampoule is frozen by generally known methods, for example by spinfreezing, and lyophilised. On completion of lyophilisation, the multidose ampoules are sealed under sterile conditions with rubber stoppers and aluminum caps.

In order to prepare an injectable solution from the dry ampoule, the lyophilisate is dissolved in 10 ml of sterile solvent. The solvent consists of an aqueous solution of tris-(hydroxymethyl)-aminomethane or of any other suitable organic base, the base having to be used in such a quantity that the injectable solution has a pH-value of from 4.0 to 4.5. 1 dry ampoule contains 1.23 g of D-penicillamine HCl corresponding to 1.0 g of D-penicillamine.

EXAMPLE 5

Production of D-Penicillamine Suppositories 300 g of D-penicillamine are worked into 1700 g of molten suppository compound (for example Hartfett DAB 7, generally with a hydroxy number of 1 to 15 preferably 2 to 5) and then poured in known manner into moulds for 2.0 g suppositories. 1 suppository contains 300 mg of D-penicillamine.

EXAMPLE 6

Production of a D-Penicillamine Ointment 50 g of D-penicillamine are dissolved in 660 g of demineralised water. The solution is introduced with continuous stirring into a melt consisting of 125 g of Emulsan MD,[1] 14 g of Lanette E[2] and 15 g of Cetiol V.[3] Stirring is contained until an ointment with the active principle homogeneously distributed in it is formed. 5 g of D-penicillamine are genuinely dissolved in 100 g of ointment.
[1]Mixture of mono- and di-glycerides of palmitic and stearic acid
[2]Sodium cetyl stearyl sulphate
[3]Decyl oleate.

EXAMPLE 7

Production of an Inhalation Solution 100 g of D-penicillamine are dissolved under gentle heat on a water bath is distilled water, in which 0.5 g of the disodium salt and ethylene diaminotetra-acetic acid and 0.5 g of sodium metabisulphite have previously been dissolved under nitrogen, up to a total volume of 1000 ml. The solution is passed through a sterilising filter and introduced under nitrogen into 50 ml bottles. 1 ml of inhalation solution contains 50 mg of D-penicillamine.

EXAMPLE 8

Production of Gelatin Insertion Capsules with D-Penicillamine and Salicylamide 185 g of D-penicillamine HCl, 75 g of mannitol and 500 g of salicylamide are mixed and granulated in known manner with 150 g of a solution consisting of 5% of hydroxypropylmethyl cellulose, 75% by weight-/volume of ethanol and 20% of demineralised water. The dried granulate is packed into gelatin insertion capsules in individual quantities of 700 mg. 1 capsule contains 185 mg of D-penicillamine HCl and 500 mg of salicylamide.

The entire disclosure of German priority application No. P.3520624.1 is hereby incorporated by reference.

The process of the invention can be used to treat humans and other animals, e.g., dogs, cats, horses, and cattle having immune deficiency illnesses.

What is claimed is:

1. A process for inhibiting the replication of a retrovirus of type HIV (Human Immunodeficiency Virus) in an animal comprising the administering to the animal an amount of penicillamine sufficient to inhibit replication of the virus.

2. A process for treating a human being having an infection of a retrovirus of type HIV (Human Immunodeficiency Virus) comprising administering to the being an amount of penicillamine sufficient to inhibit replication of the virus.

3. A process according to claim 2, wherein the penicillamine administered is D-penicillamine.

4. A process according to claim 2, wherein the penicillamine administered is L-penicillamine.

5. A process for treating a human being having an infection of a retrovirus of type HIV (Human Immunodeficiency Virus), but not exhibiting the full clinical symptoms of AIDS (Acquired Immune Deficiency Syndrome), comprising administering to the being an amount of penicillamine sufficient to inhibit replication of the virus.

6. A process according to claim 5, wherein the penicillamine administered is D-penicillamine.

7. A process according to claim 5, wherein the penicillamine administered is L-penicillamine.

* * * * *